United States Patent
Fan et al.

(10) Patent No.: US 11,246,555 B2
(45) Date of Patent: Feb. 15, 2022

(54) SYSTEMS AND METHODS FOR AUTOMATIC TUBE POTENTIAL SELECTION IN DUAL ENERGY IMAGING

(71) Applicant: GE Precision Healthcare LLC, Milwaukee, WI (US)

(72) Inventors: Jiahua Fan, New Berlin, WI (US); Zhoubo Li, Libertyville, IL (US); Mingye Wu, Glenville, NY (US); Ryan Lemminger, New Berlin, WI (US); Priti Madhav, Brookfield, WI (US); Rajeshwari Karthikeyan, Nashotah, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 228 days.

(21) Appl. No.: 16/415,941

(22) Filed: May 17, 2019

(65) Prior Publication Data
US 2020/0359987 A1 Nov. 19, 2020

(51) Int. Cl.
*A61B 6/00* (2006.01)
*G01N 23/046* (2018.01)
(Continued)

(52) U.S. Cl.
CPC .............. *A61B 6/544* (2013.01); *A61B 6/405* (2013.01); *A61B 6/482* (2013.01); *A61B 6/488* (2013.01); *A61B 6/545* (2013.01); *A61B 6/032* (2013.01); *G01N 23/046* (2013.01); *G01N 2223/423* (2013.01); *G06T 11/008* (2013.01); *G06T 2211/408* (2013.01)

(58) Field of Classification Search
CPC ......... A61B 6/482; A61B 6/488; A61B 6/544; A61B 6/032; A61B 6/405; A61B 6/545
See application file for complete search history.

(56) References Cited

U.S. PATENT DOCUMENTS

2003/0091142 A1* 5/2003 Li ........................ A61B 6/032
378/8
2007/0076842 A1* 4/2007 Tkaczyk .............. A61B 6/4042
378/5

(Continued)

FOREIGN PATENT DOCUMENTS

WO    2013049818 A1    4/2013

OTHER PUBLICATIONS

Jin, Y. et al., "CNR Analysis of Dual Energy Technologies," Proceedings of the Third International Conference on Image Formation in X-Ray Computed Tomography 2014, Jun. 22, 2014, Salt Lake City, Utah, 5 pages.

(Continued)

*Primary Examiner* — Chih-Cheng Kao
(74) *Attorney, Agent, or Firm* — McCoy Russell LLP

(57) ABSTRACT

Methods and systems are provided for dual energy imaging. In one embodiment, a method for a dual energy imaging system comprises determining a first tube potential and a second tube potential according to a size of a subject, and controlling the dual energy imaging system with the first tube potential and the second tube potential to generate lower energy x-rays and higher energy x-rays respectively to image the subject. In this way, image quality may be increased while minimizing dose during dual energy imaging of a particular imaging subject.

18 Claims, 4 Drawing Sheets

(51) Int. Cl.
*G06T 11/00* (2006.01)
*A61B 6/03* (2006.01)

(56) References Cited

U.S. PATENT DOCUMENTS

| | | | | |
|---|---|---|---|---|
| 2010/0189212 | A1* | 7/2010 | Zou | G06T 11/005 |
| | | | | 378/5 |
| 2010/0303196 | A1* | 12/2010 | Zou | A61B 6/542 |
| | | | | 378/5 |
| 2012/0114093 | A1* | 5/2012 | Yu | A61B 6/481 |
| | | | | 378/8 |
| 2014/0177788 | A1 | 6/2014 | Stevens et al. | |
| 2017/0209105 | A1* | 7/2017 | Fan | A61B 6/5205 |

OTHER PUBLICATIONS

Jin, Y. et al., "Design and Optimization of Direct-Conversion Photon-Counting Detector for Dual-Energy CT Imaging," Proceedings of the 2016 IEEE Nuclear Science Symposium, Medical Imaging Conference and Room-Temperature Semiconductor Detector Workshop (NSS/MIC/RTSD), Oct. 29, 2016, Strasbourg, France, 3 pages.

European application 20175106.2 filed May 15, 2020—Extended Search Report dated Sep. 7, 2020; 7 pages.

Japanese Patent Office, Office Action Issued in Application No. 2020-083863, dated Oct. 12, 2021, 11 pages. (Submitted with Machine Translation).

* cited by examiner

SYSTEMS AND METHODS FOR AUTOMATIC TUBE POTENTIAL SELECTION IN DUAL ENERGY IMAGING

FIELD

Embodiments of the subject matter disclosed herein relate to non-invasive diagnostic imaging, and more particularly, to dual energy imaging with automatic tube potential selection.

BACKGROUND

Dual or multi-energy spectral computed tomography (CT) systems can reveal the densities of different materials in an object and generate images acquired at multiple polychromatic x-ray energy levels. In the absence of object scatter, a system derives the behavior at a different energy based on a signal from two energy spectra: the low-energy and the high-energy incident x-ray spectra. In a given energy region of medical CT, two physical processes dominate the x-ray attenuation: Compton scattering and the photoelectric effect. The detected signals from two energy regions provide sufficient information to resolve the energy dependence of the material being imaged. Detected signals from the two energy regions provide sufficient information to determine the relative composition of an object composed of two hypothetical materials.

BRIEF DESCRIPTION

In one embodiment, a method for a dual energy imaging system comprises determining a first tube potential and a second tube potential according to a size of a subject, and controlling the dual energy imaging system with the first tube potential and the second tube potential to generate lower energy x-rays and higher energy x-rays respectively to image the subject. In this way, image quality may be increased while minimizing dose during dual energy imaging of a particular imaging subject.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
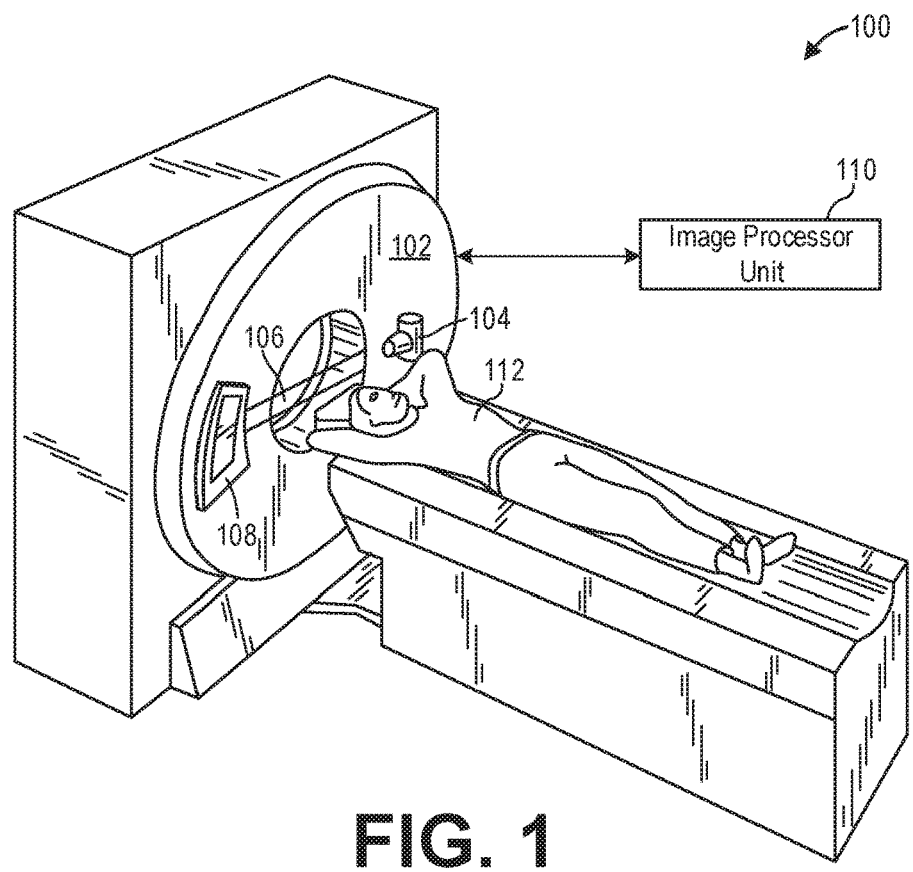
FIG. 1 shows a pictorial view of an imaging system according to an embodiment.

The following description relates to various embodiments of medical imaging systems. In particular, systems and methods are provided for dual energy imaging wherein the dual energies are tailored to the subject or object to be imaged. An example of a CT imaging system that may be used to acquire images processed in accordance with the present techniques is provided in FIGS. 1 and 2. Different approaches have been developed to realize dual energy or spectral imaging. To name a few, dual x-ray source and detector, single x-ray source and detector with multiple acquisitions at different peak kilovoltage (kVp) or interleaved with fast kVp switching capability, and single x-ray source with an energy discriminative detector are leading techniques. In a single x-ray source and detector arrangement, a conventional third generation CT system may acquire projections sequentially at different kVp levels, which changes the peak and spectrum of energy of the incident photons comprising the emitted x-ray beams. Two scans are acquired—either back-to-back sequentially in time where the scans require two rotations around the subject, hereinafter referred to as rotate-rotate dual energy, or interleaved as a function of the rotation angle requiring one rotation around the subject, hereinafter referred to as fast-switching dual energy, in which the x-ray tube operates, typically, at 80 kVp and 140 kVp potentials.

Once dual or multi-energy data is obtained, a basis material decomposition (BMD) algorithm may be applied in order to image two distinct materials, such as water and iodine, as examples. A conventional BMD algorithm is based on the concept that, in an energy region for medical CT, the x-ray attenuation of any given material can be represented by a proper density mix of two materials with distinct x-ray attenuation properties, referred to as the basis materials. The BMD algorithm computes two material density images that represent the equivalent density of one of the basis materials based on the measured projections at high and low x-ray photon energy spectra, respectively. The material density images may be further converted to form monochromatic images at other desired monochromatic energies and other additional material images.

Conventionally, the tube potentials for dual energy imaging are fixed at 80 kVp and 140 kVp, for example, regardless of the size of the imaging subject. To improve the material separability as well as increase the image quality and contrast-to-noise ratio (CNR), a method for dual energy imaging such as the method depicted in FIG. 3 includes automatically selecting a pair of tube potentials, which determines the two different x-ray spectra, based on a size of the imaging subject. For example, when imaging a particularly small subject, one or more of the tube potentials may be reduced with respect to typical or default tube potentials used for dual energy imaging. Similarly, when imaging a particularly large subject, one or more of the tube potentials may be increased with respect to typical tube potentials. To further improve the image quality, a method for dual energy imaging such as the method depicted in FIG. 4 includes automatically selecting tube potentials and tube currents, which control the dose of an imaging session, based on the size of the imaging subject as well as an imaging task or a clinical task. For example, different clinical tasks may require a different dose or a different image contrast, and the tube potentials and/or tube currents may be selected to achieve the best image quality while meeting the target dose and/or target contrast. FIG. 5 depicts example tube potential selections for different sized patients.

Though a CT system is described by way of example, it should be understood that the present techniques may also be useful when applied to images acquired using other imaging modalities, such as tomosynthesis, MRI, C-arm angiography, and so forth. The present discussion of a CT imaging modality is provided merely as an example of one suitable imaging modality.

FIG. 1 illustrates an exemplary CT system 100 configured for dual energy imaging with automatic tube potential selection. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 for use in imaging the subject 112. Specifically, the x-ray radiation source 104 is configured to project the x-rays 106 towards a detector array 108 positioned on the opposite side of the gantry 102. Although FIG. 1 depicts only a single x-ray radiation source 104, in certain embodiments, multiple x-ray radiation sources and detectors may be employed to project a plurality of x-rays 106 for acquiring projection data corresponding to the patient at different energy levels. In some embodiments, the x-ray radiation source 104 may enable dual-energy gemstone spectral imaging (GSI) by rapid kVp switching. In some embodiments, the x-ray detector employed is a photon-counting detector which is capable of differentiating x-ray photons of different energies. In other embodiments, two sets of x-ray tube-detector are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered backprojection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach. Further, in some examples, the image processor unit 110 is configured to reconstruct images of a target volume of the subject 112 using artificial intelligence (AI) image reconstruction or deep learning image reconstruction (DLIR) methods.

In some known CT imaging system configurations, a radiation source projects a cone-shaped beam which is collimated to lie within an X-Y-Z plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused embodiments.

The projection data is processed to reconstruct an image that corresponds to a two-dimensional slice taken through the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation-reconstruction techniques as well as iterative reconstruction techniques and AI/DL reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 2:
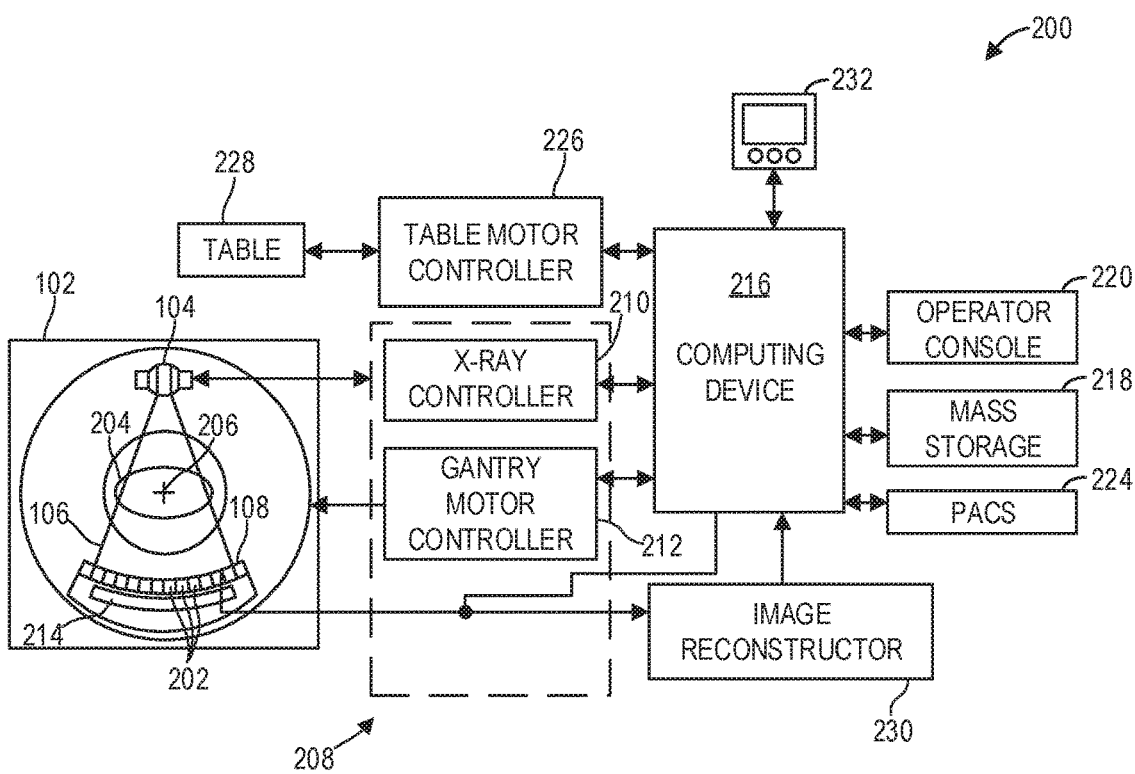
FIG. 2 shows a block schematic diagram of an exemplary imaging system according to an embodiment.

FIG. 2 illustrates an exemplary imaging system 200 similar to the CT system 100 of FIG. 1. In accordance with aspects of the present disclosure, the imaging system 200 is configured for dual energy imaging with automatic selection of tube potentials. In one embodiment, the imaging system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In dual or multi-energy imaging, two or more sets of projection data are typically obtained for the imaged object at different tube kilovoltage (kVp) levels, which change the maximum and spectrum of energy of the incident photons comprising the emitted x-ray beams or, alternatively, at a single tube kilovoltage (kVp) level or spectrum with an energy resolving detector of the detector array 108. As discussed further herein with regard to FIGS. 3 and 4, the computing device 216 of the imaging system 200 may be configured to automatically select two or more tube kVp levels or tube kV levels for dual or multi-energy imaging of the imaged object, wherein the two or more tube kVp levels or tube kV levels are selected based on the size of the imaged object to increase spectral dose efficiency and image quality.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computer or computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 200 either includes or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may comprise a motorized table. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in imaging system 200. In one embodiment, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

Figure 3:
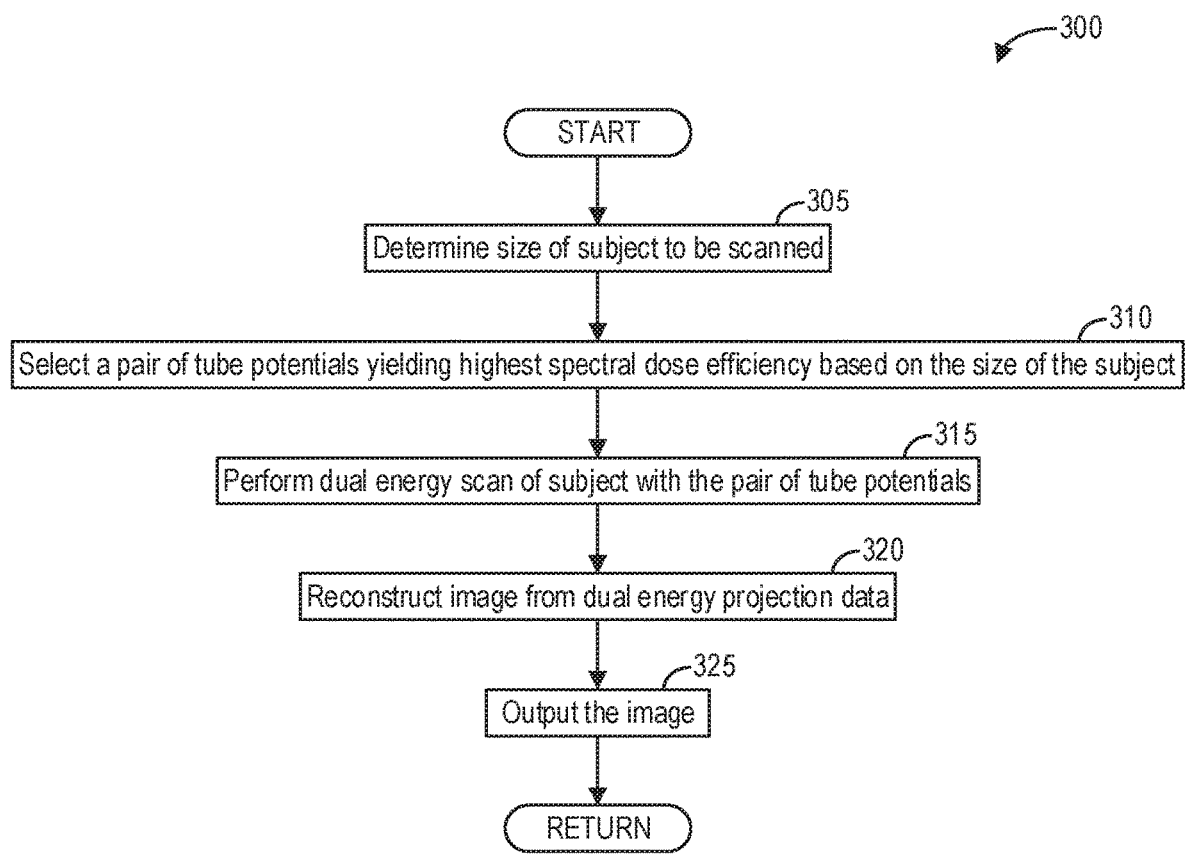
FIG. 3 shows a high-level flow chart illustrating an example method for dual energy imaging with automatic tube potential selection according to an embodiment.

FIG. 3 shows a high-level flow chart illustrating an example method 300 for dual energy imaging with automatic tube potential selection according to an embodiment. Method 300 is described with regard to the systems and components of FIGS. 1 and 2, though it should be appreciated that the method 300 may be implemented with other systems and components without departing from the scope of the present disclosure. Method 300 may be implemented as executable instructions in non-transitory memory of one or more computing devices, such as the image reconstructor 230 and/or the computing device 216.

Method 300 begins at 305. At 305, method 300 determines the size of a subject to be scanned. To determine the size of the subject, method 300 may perform one or more scout scans of the subject. The scout scan may comprise a low-dose single-energy CT scan of the subject, and scout projection data acquired during the scout scan may be used primarily to localize the scan range for the full scan. In addition, the size and shape of the subject may be determined or estimated from the scout data. As one example, a size or depth of the subject along at least one direction may be measured directly from the projection data without scout image reconstructions, or alternatively may be measured from a scout image reconstructed from the scout projection data in a particular imaging plane (e.g., sagittal, coronal, or axial) depending on the desired direction of the depth. As another example, the size of the subject may be expressed in terms of a water-equivalent diameter, which may be calculated based on CT numbers of the scout projection data. In some examples, a single size may be determined for the subject, though it should be appreciated that in some examples, the shape of the subject may be determined, for example by measuring the size of the subject at a plurality of projection angles.

In other examples, a user or operator of the imaging system may input the size of the subject to be imaged, for example via a user input device of the operator console 220. For example, the operator of the imaging system may estimate or manually measure the size of the subject to be imaged, and input the size of the subject via the operator console 220. In such examples, method 300 receives the size of the subject input by the operator or user via the operator console 220. Alternatively, method 300 may receive quantitative measurements of the subject such as height and/or weight and may estimate the size and/or shape of the subject according to the height and/or weight. In yet other examples, method 300 may determine the size of the subject by analyzing one or more photographs of the subject captured via an optical camera, by retrieving the size of the subject from a database, by determining the size of the subject from previously-acquired scout scans or diagnostic scans, and so on.

After determining the size of the subject, method 300 continues to 310. At 310, method 300 selects a pair of tube potentials yielding the largest spectral dose efficiency based on the size of the subject. The pair of tube potentials comprises a first, lower tube potential and a second, higher tube potential for applying to the x-ray source 104 to generate lower energy photons and higher energy photons, respectively, for dual energy imaging of the subject 206. The pair of tube potentials may comprise a tube voltage (expressed as kilovoltage or kV) or alternatively may comprise a maximum tube voltage or peak kilovoltage (kVp) applied across the x-ray source 104. The first tube potential may be selected from a first plurality of tube potentials, ranging from 60 kV to 100 kV, while the second tube potential may be selected from a second plurality of tube potentials, ranging from 110 kV to 160 kV, as illustrative and non-limiting examples. As illustrative example, the first tube potential may comprise 70 kV while the second tube potential may comprise 130 kV for a smaller subject, for example with a 10 centimeter depth. In contrast, the first tube potential may comprise 80 kV while the second tube potential may comprise 140 kV for a larger subject, for example with a 40 centimeter depth.

Method 300 may select the pair of tube potentials by retrieving the pair of tube potentials from a lookup table. For example, the lookup table may provide an optimal pair of tube potentials for a given size of the subject. Thus, method 300 may retrieve a pair of tube potentials corresponding to the size of the subject determined at 305.

The lookup table may be prepared by systematically imaging a plurality of phantoms of different sizes, for example, with a plurality of pairs of tube potentials for each size, reconstructing images from the acquired data, and determining the energy separation and dose efficiency performance of each pair of tube potentials by evaluating the noise distribution in the images. The images reconstructed from the acquired data may comprise basis material images and/or monochromatic images generated after material decomposition, such that the evaluation of the images accounts for the amplification of noise after material decomposition. Evaluating the noise distribution in the images may comprise measuring the contrast-to-noise (CNR) ratio. More specifically, the performance of each pair of tube potentials may be quantitatively evaluated according to the spectral dose efficiency which corresponds to the CNR squared, which indicates the material separability at the given dose level. Thus, in some examples, the lookup table may include, for each size, a pair of tube potentials which yielded the highest spectral dose efficiency and therefore the best performance during the systematic imaging of the phantoms. For a certain sized object, the spectral dose efficiency is a measure of the CNR per dose for a given pair of tube potentials and a given pair of tube currents used in dual energy imaging. The higher the value of the spectral dose efficiency, the larger the estimated CNR. As such, a higher spectral dose efficiency value suggests the corresponding imaging parameters uses less dose to achieve the target image quality.

It should be appreciated that while spectral dose efficiency is described herein as the metric for automatic selection of tube potentials, other quantitative metrics relating to dose, image contrast, image noise, and so on may be utilized without departing from the scope of the present disclosure.

Figure 4:
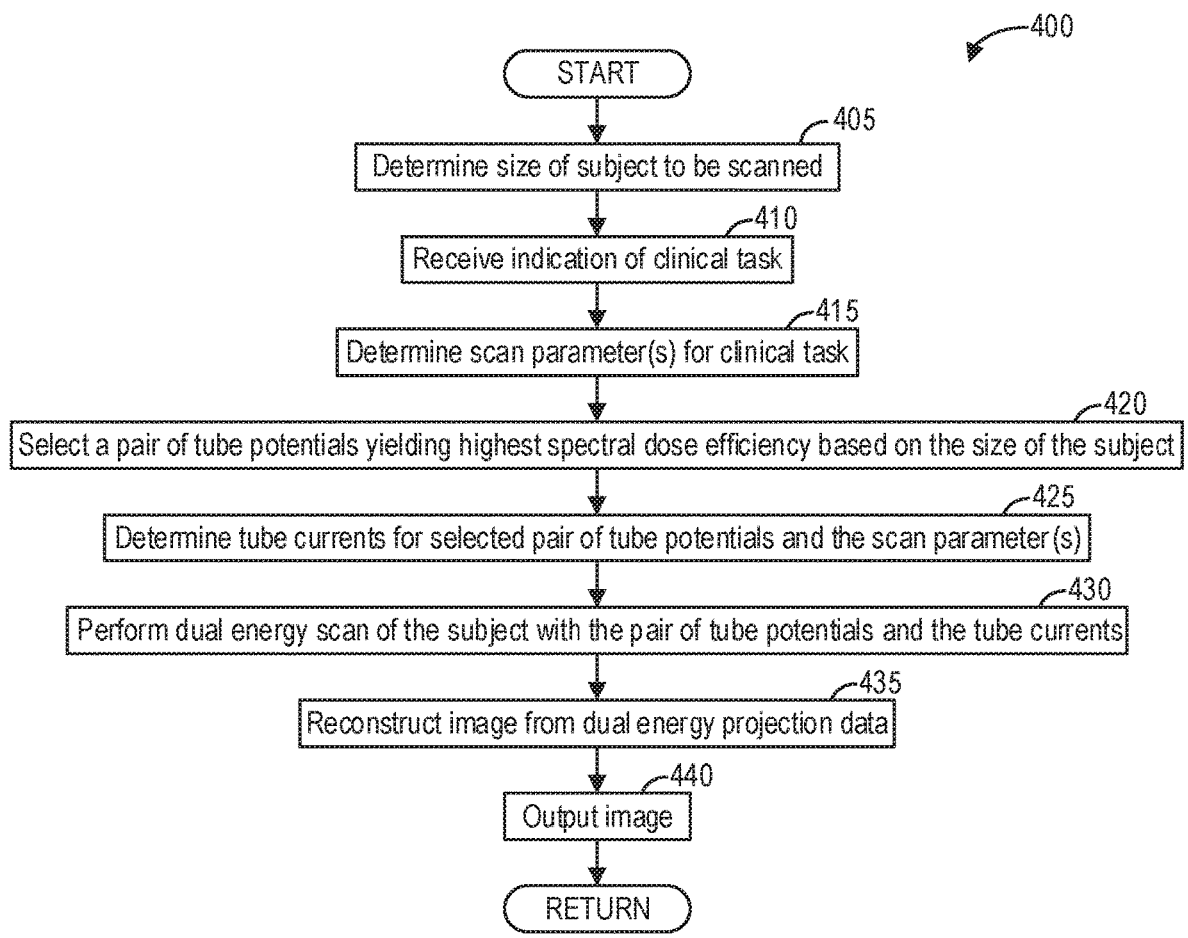
FIG. 4 shows a high-level flow chart illustrating an example method for dual energy imaging with automatic tube potential and tube current selection according to an embodiment.
Figure 5:
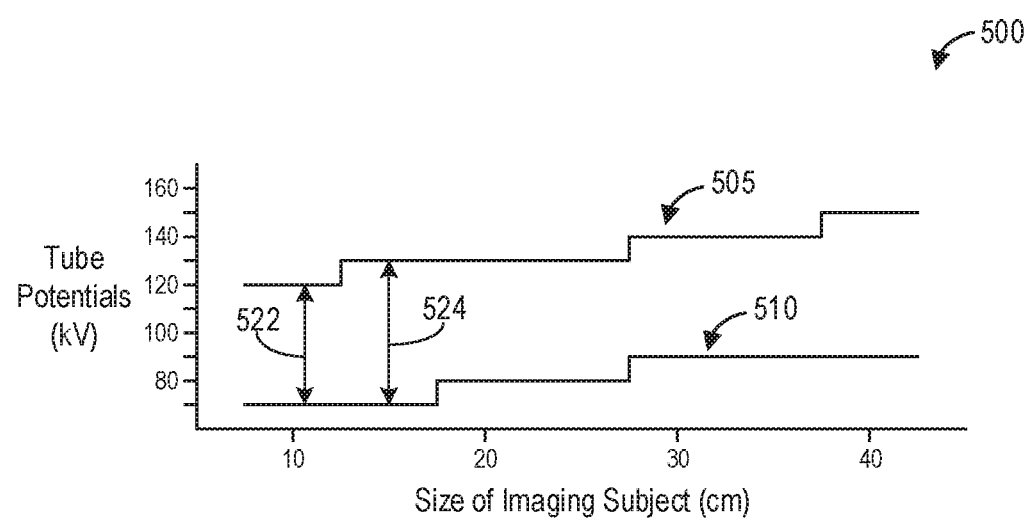
FIG. 5 shows a graph illustrating example pairs of tube potentials for different sized imaging subject according to an embodiment.

In addition, as discussed further herein with regard to FIG. 4, the lookup table may include additional dimensions relating to dose as well as the balance of dose between higher and lower tube potentials. In this way, the pair of tube potentials may be automatically selected via the lookup table to achieve the best image noise performance for the size of the subject as well as the desired dose for the subject.

In some examples, method 300 displays the selected pair of tube potentials to the operator of the imaging system, for example via the display 232, as recommended tube potentials. The operator may then select the pair of tube potentials for dual energy imaging of the subject, for example via the operator console 220, or the operator may input adjustments to the pair of tube potentials. For example, the operator may input, via the operator console 220, a pair of tube potentials for dual energy imaging of the subject that is different from the pair of tube potentials selected by method 300. Therefore, although the pair of tube potentials automatically selected by method 300 may be optimal for imaging the particular subject, method 300 may further enable a manual confirmation of the selection as well as manual adjustments to the selection.

After selecting the pair of tube potentials at 310, method 300 continues to 315. At 315, method 300 performs a dual energy scan of the subject with the pair of tube potentials. For example, method 300 controls the x-ray source 104 with the first, lower tube potential and the second, higher tube potential in accordance with a dual energy imaging technique to generate x-ray beams with lower energy photons and higher energy photons directed towards the subject, and acquires corresponding lower energy projection data and higher energy projection data via the detector array 108. It should be appreciated that the automatically-selected pair of tube potentials may be used to control the imaging system with any suitable dual energy imaging technique, including but not limited to a fast kV switching, dual source and dual detector, dual layer detector, slow kV switching, and so on.

At 320, method 300 reconstructs an image from dual energy projection data acquired during the dual energy scan. Method 300 may reconstruct one or more images, including but not limited to one or more of basis material images (for example, a water image and an iodine image from a basis material decomposition of the dual energy projection data), a low energy image (for example, from the lower energy projection data), a high energy image (for example, from the higher energy projection data), a polychromatic image, and a monochromatic image. It should be appreciated that the accuracy of basis material decomposition and thus the accuracy of material density images and calculations may be increased due to the optimization of the tube potentials. Furthermore, for a monochromatic image reconstructed from the dual energy projection data, the noise distribution may be minimized due to the selection of the tube potentials.

Continuing at 325, method 300 outputs the image. For example, method 300 may output the image to the display 232 for display to the operator. Additionally or alternatively, method 300 may output the image to mass storage 218 and/or PACS 224 for subsequent retrieval and review. Method 300 then returns.

Thus, a method is provided for a dual energy imaging system, the method comprising determining a first tube potential and a second tube potential according to a size of a subject, and controlling the dual energy imaging system with the first tube potential and the second tube potential to generate lower energy x-rays and higher energy x-rays respectively to image the subject. The method further comprises acquiring a lower energy projection data and higher energy projection data corresponding to the lower energy x-rays and the higher energy x-rays attenuated respectively by the subject, and reconstructing an image from the lower energy projection data and the higher energy projection data. By automatically tailoring tube potentials or kV pairs to the imaging subject, the image quality of the reconstructed image(s) and the spectral dose efficiency for spectral CT imaging is increased. This increase in image quality and spectral dose efficiency is especially notable in contrast with previous approaches of using default tube potentials regardless of the size of the imaging subject. Furthermore, by providing a systematic and automatic technique for the selection of an optimal pair of tube potentials, poor image quality and excessive dose potentially caused by human error in the manual adjustments of imaging parameters is avoided.

In addition to automatically selecting a pair of tube potentials for dual energy imaging, in some examples a pair of corresponding tube currents may be automatically selected for maximizing the image quality and spectral dose efficiency while maintaining a target dose. As an illustrative example, FIG. 4 shows a high-level flow chart illustrating an example method 400 for dual energy imaging with automatic tube potential and tube current selection according to an embodiment. Method 400 is described with regard to the systems and components of FIGS. 1 and 2, though it should be appreciated that the method 400 may be implemented with other systems and components without departing from the scope of the present disclosure. Method 400 may be implemented as executable instructions in non-transitory memory of one or more computing devices, such as the image reconstructor 230 and/or the computing device 216, and when executed the method 400 may cause the computing device 216 for example to perform the actions described herein.

Method 400 begins at 405. At 405, method 400 determines a size of a subject to be scanned. For example, the size and shape of the subject may be determined or estimated from scout projection data. In such an example, method 400 performs a scout scan of the subject. The scout scan may comprise a low-dose single-energy CT scan of the subject, and scout projection data acquired during the scout scan may be used primarily to localize the scan range for the full scan. A size or depth of the subject along at least one direction may then be measured directly from the projection data without scout image reconstructions, or alternatively may be measured from a scout image reconstructed from the scout projection data in a particular imaging plane (e.g., sagittal, coronal, or axial) depending on the desired direction of the depth. As another example, the size of the subject may be expressed in terms of a water-equivalent diameter, which may be calculated based on CT numbers of the scout projection data. In some examples, a single size may be determined for the subject, though it should be appreciated that in some examples, the shape of the subject may be determined, for example by measuring the size of the subject at a plurality of projection angles.

Further, in some examples the size of the subject may be determined without the use of scout projection data, as described hereinabove with regard to FIG. 3. For example, a user or operator of the imaging system may input the size of the subject to be imaged, for example via a user input device of the operator console 220. For example, the operator of the imaging system may estimate or manually measure the size of the subject to be imaged, and input the size of the subject via the operator console 220. In such examples, method 400 receives the size of the subject input by the operator or user via the operator console 220. Alternatively, method 400 may receive quantitative measurements of the subject such as height and/or weight and may estimate the size and/or shape of the subject according to the height and/or weight. In yet other examples, method 400 may determine the size of the subject by analyzing one or more photographs of the subject captured via an optical camera, by retrieving the size of the subject from a database, by determining the size of the subject from previously-acquired scout scans or diagnostic scans, and so on.

Continuing at 410, method 400 receives an indication of a clinical task. For example, the operator of the imaging system may input, via an operator console 220 as an example, an indication of the clinical task or the clinical application for the scan. As another example, an indication of the clinical task may be retrieved from a database. The clinical task may describe, for example, the portion of anatomy to be imaged or diagnosed, the type and quantity of contrast agent used, the type and size of lesion to be evaluated, and so on. Additionally or alternatively, the indication of the clinical task may comprise an indication of a task such as detection, screening, and so on.

After receiving the indication of the clinical task, method 400 continues to 415. At 415, method 400 determines one or more scan parameters for the clinical task. In one example, the one or more scan parameters includes a desired dose, and so method 400 determines a desired dose for the clinical task. For example, the clinical task prescribes a desired radiation dose or at least sets constraints on an allowable dose. For some tasks, spatial resolution may be more important, while for other tasks, the noise level may be more important. For some screening tasks, for example, the dose may be more important than the noise level, as such screenings typically use a low dose. Thus, method 400 may reference a clinical task-dose lookup table containing a set of constraints on dose levels for clinical tasks, and may retrieve a dose or a set of constraints on dose for the indicated clinical task. Additionally or alternatively, method 400 may select a target contrast based on the clinical task, or the target contrast may be determined according to the target dose. As another example, method 400 determines scan parameters in addition to dose according to the clinical task. For example, the clinical task may define or specify one or more critical-to-quality (CTQ) parameters such as spatial resolution, noise, and so on. For example, as mentioned above, the clinical task may specify a CTQ parameter such as spatial resolution, and so method 400 determines a scan parameter such as focal spot size accordingly. Additionally or alternatively, the clinical task may specify a CTQ parameter such as noise, which may set limits on the dose.

At 420, method 400 selects a pair of tube potentials yielding the highest spectral dose efficiency based at least on the size of the subject. As described hereinabove, the pair of tube potentials comprises a first, lower tube potential and a second, higher tube potential for applying to the x-ray source 104 to generate lower energy photons and higher energy photons, respectively, for dual energy imaging of the subject 206. The pair of tube potentials may comprise a pair of tube voltages (kV) or a pair of peak kilovoltages (kVp). Method 400 may select the pair of tube potentials by retrieving the pair of tube potentials from a lookup table. For example, as described hereinabove with regard to FIG. 3, the lookup table may provide a pair of tube potentials with a highest spectral dose efficiency for a given size of the subject. Thus, method 400 may retrieve a pair of tube potentials corresponding to the size of the subject determined at 405.

Furthermore, in some examples, method 400 selects the pair of tube potentials yielding the highest spectral dose efficiency based on the size of the subject and the clinical task. For example, for a subject of a given size, different pairs of tube potentials may yield the highest spectral dose efficiency for different desired doses. The lookup table may include different tables of pairs of tube potentials with a highest spectral dose efficiency for a plurality of sizes and for a plurality of target doses. For example, the first tube potential may be selected from a first plurality of tube potentials, ranging from 60 kV to 100 kV, while the second tube potential may be selected from a second plurality of tube potentials, ranging from 110 kV to 160 kV, as illustrative and non-limiting examples. As illustrative example, for a first target dose, the first tube potential may comprise 70 kV while the second tube potential may comprise 130 kV for a smaller subject, for example with a 10 centimeter depth, whereas the first tube potential may comprise 80 kV while the second tube potential may comprise 140 kV for a larger subject, for example with a 40 centimeter depth. In contrast, for a second target dose lower than the first target dose, the pair of tube potentials that provide the highest spectral dose efficiency may comprise 80 kV and 130 kV for a smaller subject with a 10 centimeter depth, whereas the pair of tube potentials providing the highest spectral dose efficiency may comprise 90 kV and 150 kV for a larger subject with a 40 centimeter depth. The lookup table described herein may provide measurements of spectral dose efficiency, for example, for each combination of tube potentials and for each size of an imaging subject, and may further provide such measurements for a range of target doses.

Continuing at 425, method 400 determines tube currents for the selected pair of tube potentials and the one or more scan parameters determined according to the clinical task. As an example, method 400 selects a first tube current and a second tube current for driving the x-ray source 104 with the first tube potential and the second tube potential, respectively, to achieve the desired dose. For example, as the tube potentials determine the energy of the photons emitted by the x-ray source 104, the tube currents determine the number of photons emitted by the x-ray source 104 in a given duration. Therefore, the first tube current is selected such that the x-ray source 104 generates a first dose with the first tube current and the first tube potential, and the second tube current is selected such that the x-ray source 104 generates a second dose with the second tube current and the second tube potential, wherein the first dose and the second dose amount to the desired dose when combined.

Further, in some examples, method 400 determines a first tube current profile and a second tube current profile for driving the x-ray source 104 with the first tube potential and the second tube potential respectively, to achieve a desired dose according to varying attenuation of the imaging subject. For example, tube current modulation techniques such as automatic exposure control (AEC) may be used to determine a first tube current profile comprising a first set of tube currents as well as a second tube current profile comprising a second set of tube currents, wherein each tube current of the first and second sets of tube currents provides the desired dose in combination with the first and second tube potentials at each position along a length of the imaging subject. The varying attenuation of the imaging subject may be determined, for example, according to varying depths of the imaging subject derived from scout scan data. Method 400 may therefore select a first and second tube current for each depth of the imaging subject along the length of the imaging subject to be scanned. Additionally or alternatively, the computing device 216 or the x-ray controller 210 may estimate the varying attenuation of the imaging subject in real-time during a scan, and select an appropriate tube current for driving the x-ray source 104 to provide the desired dose for both the first and second tube potentials.

In some examples, the tube currents may be selected assuming a balanced dose between the first tube potential and the second tube potential. For example, the first tube current and the second tube current may be selected such that the first dose and the second dose are equal.

In other examples, method 400 may adjust the relative doses for the first tube potential and the second tube potential to achieve the highest spectral dose efficiency. For example, method 400 may select the first tube potential and the second tube potential at 420 via the lookup table for the size of the subject, based on which pair of tube potentials yields the highest spectral dose efficiency for the size of the subject. The lookup table may further include corresponding tube currents for each pair of tube potentials, as well as measurements of the spectral dose efficiency for different ratios of doses between the first and second tube potentials. Method 400 may therefore select tube currents corresponding to the tube potentials which yields the highest spectral dose efficiency.

As an illustrative example, larger subjects may attenuate lower energy photons more easily, such that increasing the dose of the lower energy photons relative to the dose of the higher energy photons may provide a better spectral dose efficiency than balancing the dose between the lower and higher energy photons. In such an example, method 400 may select a first tube current and a second tube current such that the first dose (i.e., the dose of the lower energy photons at the first tube potential) is greater than the second dose (i.e., the dose of the higher energy photons at the second tube potential).

Thus, in addition to selecting a first tube potential and a second tube potential that provide the highest spectral dose efficiency for a given size of a subject, method 400 also selects a first tube current and a second tube current to achieve the desired dose while providing the highest spectral dose efficiency. The lookup table described herein may provide measurements of spectral dose efficiency for each pair of tube potentials for different sizes of imaging subjects and different target doses, as well as for different pairs of tube currents and different ratios of tube currents (for example, ranging from 30% dose to 70% dose assigned to the lower tube potential). Further, as mentioned above, a target contrast may be selected according to the dose and/or the clinical task, and the pair of tube currents may also be determined at least in part based on the target contrast. In this way, the pair of tube potentials and the pair of corresponding tube currents may be specially tailored for a given imaging subject and a given clinical task.

After selecting a pair of tube currents for the selected pair of tube potentials and the desired dose, method 400 continues to 430. At 430, method 400 performs a dual energy scan of the subject with the pair of tube potentials and the tube currents. For example, method 400 controls the x-ray source 104 via the x-ray controller 210 with the first tube current and the first tube potential to generate first beam(s) of x-rays or photons at the first, lower energy level, and further with the second tube current and the second tube potential to generate second beam(s) of x-rays at the second, higher energy level, and acquires, via the detector array 108, a set of lower energy projection data and a set of higher energy projection data respectively corresponding to the first beam (s) and the second beam(s) attenuated by the subject. It should be appreciated that in some examples, method 400 controls the x-ray source 104 with a first tube current profile including at least the first tube current along with the first tube potential to generate the first beam(s) of x-rays at the first, lower energy level, and further with a second tube current profile including at least the second tube current along with the second tube potential to generate the second beam(s) of x-rays at the second, higher energy level.

The particular control of the x-ray source 104 during the dual energy scan of the subject depends on the particular implementation of the dual energy imaging technique. For example, for rapid kVp switching, method 400 may rapidly switch between the first tube potential (and first tube current) and the second tube potential (and the second tube current). As another example, for embodiments wherein multiple x-ray sources 104 are used, a first x-ray source 104 may be driven with the first tube potential and the first tube current while a second x-ray source may be driven with the second tube potential and the second tube current.

At 435, method 400 reconstructs an image from the dual energy projection data. For example, method 400 may apply a basis material decomposition to the lower energy projection data and the higher energy projection data to obtain a first basis material projection data set (e.g., corresponding to water) and a second basis material projection data set (e.g., corresponding to iodine), reconstruct a first basis material image and a second basis material image from the first and second basis material projection data sets respectively, and generate a monochromatic image from the first and second basis material images. Additionally or alternatively, method 400 may reconstruct a lower energy image from the lower energy projection data and/or a higher energy image from the higher energy projection data. Other material density images can also be generated from the basis material images. It should be appreciated that any number of techniques for processing dual energy projection data, including noise and artifact reduction techniques, may be applied to the projection data, and furthermore that any number or types of images suitable for diagnostic purposes or other purposes may be reconstructed from the projection data.

At 440, method 400 outputs the image. For example, method 400 outputs the image to a display 232 for review by an operator of the imaging system 200, and/or outputs the image to mass storage 218 and/or PACS 224 for subsequent retrieval and review. The image output by method 400 may comprise one or more of the images reconstructed at 435, including one or more of the monochromatic image, the basis material images, the higher energy image, the lower energy image, and so on. Method 400 then returns.

Thus, a method for a dual energy imaging system comprises determining a size of a subject to be imaged, determining a dose according to a clinical task for imaging the subject, selecting a pair of tube potentials to obtain a highest spectral dose efficiency for the size of the subject, determining a pair of tube currents for the pair of tube potentials according to the dose, performing a dual energy scan of the subject with the pair of tube currents and the pair of tube potentials, and reconstructing an image from dual energy projection data acquired during the dual energy scan.

It should be appreciated that method 400 is illustrative and non-limiting. For example, although FIG. 4 depicts each action of method 400 occurring in a specific sequence or serially, the actions of method 400 may be ordered differently and/or one or more actions may be performed in parallel or even repeated without departing from the scope of the present disclosure. For example, in some examples, method 400 may receive the indication of the clinical task at 410 and determine the dose for the clinical task at 415 prior to determining the size of the subject to be scanned at 405. As mentioned above, method 400 may determine tube currents in real-time during the dual energy scan to dynamically adapt the tube currents to varying attenuation levels of the imaging subject. Further, in some examples, method 400 may select a plurality of pairs of tube potentials yielding a highest spectral dose efficiency based on such varying depths along a length of the imaging subject, and method 400 may perform such a selection prior to or even during the dual energy scan of the subject. Further, while method 400 depicts selecting the pair of tube potentials prior to determining the tube currents, it should be appreciated that method 400 may select the pair of tube potentials and determine the tube currents simultaneously. For example, as discussed hereinabove, the selection of tube potentials and tube currents both determine the dose and so the selection is based on the size of the subject, and furthermore both the tube potentials and tube currents may be stored in a same lookup table. Therefore, while the actions 420 and 425 are depicted as separate actions, in some examples selecting the pair of tube potentials and the corresponding pair of tube currents or tube current profiles may be performed as a single action or in parallel.

To illustrate the selection of different tube potentials for imaging subjects of a different size, FIG. 5 shows a graph 500 illustrating example pairs of tube potentials for imaging subjects of different sizes. In particular, graph 500 comprises a visual depiction of pairs of tube potentials stored in a lookup table as described hereinabove for a given target dose, wherein the pairs of tube potentials depicted provide the highest spectral dose efficiency for each corresponding size. To that end, graph 500 depicts higher energy tube potentials 505 and lower energy tube potentials 510 as a function of size of the imaging subject. As depicted, for an imaging subject with a size of 10 centimeters, the higher energy tube potential 505 is 120 kV while the lower energy tube potential 510 is 70 kV. The energy separation 522 between the tube potentials 505 and 510 for a 10 centimeter imaging subject is therefore equal to 50 kV. Meanwhile, for an imaging subject with a size of 15 centimeters, the higher energy tube potential 505 is 130 kV while the lower energy tube potential 510 is 70 kV. Thus, for a slightly larger imaging subject, the higher energy tube potential 505 is increased while the lower energy tube potential 510 remains the same, such that the energy separation 524 between the tube potentials 505 and 510 is equal to 60 kV. Therefore, in some instances, a higher or lower energy separation between tube potentials 505 and 510 may provide an improved spectral dose efficiency in comparison to other pairs of tube potentials at different sizes.

Further, as depicted, the lower energy tube potential 510 increases to 80 kV for an imaging subject with a size of 20 centimeters, while the higher energy tube potential 505 remains at 130 kV, such that the energy separation is 50 kV. The tube potentials 505 and 510 remain unchanged for imaging subjects with a size of 25 centimeters, as this pair of tube potentials provides a highest spectral dose efficiency for imaging subjects with sizes of 20 centimeters and 25 centimeters. In this way, the pairs of tube potentials providing a highest spectral dose efficiency may be the same for at least some sizes of an imaging subject.

The lower energy tube potential 510 increases to 90 kV while the higher energy tube potential 505 increases to 140 kV for imaging subjects with sizes ranging from approximately 30 centimeters to 35 centimeters. The higher energy tube potential 505 increases to 150 kV while the lower energy tube potential 510 remains at 90 kV for imaging subjects with a size of 40 centimeters. The energy separation between the tube potentials 505 and 510 for imaging subjects with a size of 40 centimeters is 60 kV.

Thus, one or both of the tube potentials may be increased for imaging subjects of progressively larger sizes, and decreased for imaging subjects of progressively smaller sizes. Further, the energy separation between the tube potentials may differ for imaging subjects of different sizes.

It should be appreciated that the example energy separations 522 and 524, as well as the example selections of tube potentials 505 and 510, are illustrative and non-limiting, and that in practice the imaging system may automatically select or recommend different pairs of tube potentials with more or less energy separation for imaging subjects of different sizes.

A technical effect of the disclosure is the automatic selection of tube potentials for dual energy imaging of a subject. Another technical effect of the disclosure is the adjustment of tube potentials and tube currents for dual energy imaging of a subject to achieve an increased spectral dose efficiency. Yet another technical effect of the disclosure is the generation of x-rays by an x-ray source driven by tube potentials and tube currents automatically selected according to a size of a subject. Another technical effect of the disclosure includes the reconstruction of an image with an improved image quality due to automatically selected tube potentials.

In one embodiment, a method for a dual energy imaging system comprises determining a first tube potential and a second tube potential according to a size of a subject, and controlling the dual energy imaging system with the first tube potential and the second tube potential to generate lower energy x-rays and higher energy x-rays respectively to image the subject.

In a first example of the method, determining the first tube potential and the second tube potential according to the size of the subject comprises selecting the first tube potential from a first plurality of tube potentials and the second tube potential from a second plurality of tube potentials. In a second example of the method optionally including the first example, a combination of the first tube potential and the second tube potential provides a higher spectral dose efficiency for the size of the subject relative to other combinations of the first plurality of tube potentials and the second plurality of tube potentials. In a third example of the method optionally including one or more of the first and second examples, the method further comprises performing a scout scan of the subject, and determining the size of the subject based on the scout scan. In a fourth example of the method optionally including one or more of the first through third examples, the method further comprises receiving an indication of the size of the subject from an operator of the imaging system. In a fifth example of the method optionally including one or more of the first through fourth examples, the method further comprises determining a desired dose for imaging the subject. In a sixth example of the method optionally including one or more of the first through fifth examples, the method further comprises receiving an indication of a clinical task for imaging the subject, and determining the desired dose based on the clinical task. In a seventh example of the method optionally including one or more of the first through sixth examples, the method further comprises determining a first tube current and a second tube current to pair with the first tube potential and the second tube potential, respectively, for achieving the desired dose. In an eighth example of the method optionally including one or more of the first through seventh examples, determining the first tube current and the second tube current comprises selecting the first tube current and the second tube current for the first tube potential and the second tube potential, and adjusting the first tube current relative to the second tube current to provide a highest spectral dose efficiency. In a ninth example of the method optionally including one or more of the first through eighth examples, the method further comprises acquiring a lower energy projection data and higher energy projection data corresponding to the lower energy x-rays and the higher energy x-rays attenuated respectively by the subject, reconstructing an image from the lower energy projection data and the higher energy projection data, and outputting the image to one or more of a display device and a storage device.

In another embodiment, a method for a dual energy imaging system comprises determining a size of a subject to be imaged, determining a dose according to a clinical task for imaging the subject, selecting a pair of tube potentials to obtain a highest spectral dose efficiency for the size of the subject, determining a pair of tube currents for the pair of tube potentials according to the dose, performing a dual energy scan of the subject with the pair of tube currents and the pair of tube potentials, and reconstructing an image from dual energy projection data acquired during the dual energy scan.

In a first example of the method, the method further comprises selecting a first tube potential of the pair of tube potentials from a first plurality of tube potentials and a second tube potential of the pair of tube potentials from a second plurality of tube potentials, wherein tube potentials of the first plurality of tube potentials are smaller than tube potentials of the second plurality of tube potentials. In a second example of the method optionally including the first example, determining the pair of tube currents comprises determining a first tube current for the first tube potential to provide a first dose and a second tube current for the second tube potential to provide a second dose, wherein the first dose and the second dose add up to the dose. In a third example of the method optionally including one or more of the first and second examples, the method further comprises adjusting the first tube current and the second tube current to provide a higher spectral dose efficiency while maintaining the dose. In a fourth example of the method optionally including one or more of the first through third examples, the method further comprises performing a scout scan of the subject, and automatically determining the size of the subject based on scout projection data acquired during the scout scan.

In yet another embodiment, a system comprises an x-ray source that emits a beam of x-rays toward a subject to be imaged, a detector that receives the x-rays attenuated by the subject, a data acquisition system (DAS) operably connected to the detector, and a computing device operably connected to the DAS and configured with executable instructions in non-transitory memory that when executed cause the computing device to: automatically select a first tube potential and a second tube potential according to a size of the subject; control the x-ray source, during a dual energy scan of the subject, with the first tube potential and the second tube potential; acquire, via the DAS, lower energy projection data and higher energy projection data corresponding to detected photons generated by the x-ray source at the first tube potential and the second tube potential respectively and attenuated by the subject; and reconstruct an image from the lower energy projection data and the higher energy projection data.

In a first example of the system, the computing device is further configured with executable instructions that when executed cause the computing device to automatically select the first tube potential and the second tube potential to achieve a highest spectral dose efficiency for the size of the subject. In a second example of the system optionally including the first example, the computing device is further configured with executable instructions that when executed cause the computing device to automatically select a first tube current for the first tube potential and a second tube current for the second tube potential based on a target dose for a clinical task. In a third example of the system optionally including one or more of the first and second examples, the computing device is further configured with executable instructions that when executed cause the computing device to adjust the first tube current and the second tube current to increase the spectral dose efficiency while maintaining the target dose. In a fourth example of the system optionally including one or more of the first through third examples, the system further comprises a display device communicatively coupled to the computing device, and the computing device is further configured with executable instructions that when executed cause the computing device to output the image to the display device for display.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. Although the examples provided herein are related to medical application, the scope of the present disclosure covers non-destructive testing in industrial, biomedical, and other fields. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a dual energy imaging system, comprising:
   selecting an imaging protocol for a scan based on a clinical task;
   performing a scout scan of a subject and determining a size and a shape of the subject according to the scout scan;
   automatically determining a first tube potential and a second tube potential according to the size and the shape of the subject and the clinical task, wherein the size includes a height or a weight of the subject; and
   controlling the dual energy imaging system with the first tube potential and the second tube potential to generate lower energy x-rays and higher energy x-rays respectively to image the subject.

2. The method of claim 1, wherein determining the first tube potential and the second tube potential according to the size of the subject comprises selecting the first tube potential from a first plurality of tube potentials and the second tube potential from a second plurality of tube potentials.

3. The method of claim 2, wherein a combination of the first tube potential and the second tube potential provides a higher spectral dose efficiency for the size of the subject relative to other combinations of the first plurality of tube potentials and the second plurality of tube potentials.

4. The method of claim 2, further comprising determining a desired dose for imaging the subject.

5. The method of claim 4, further comprising receiving an indication of the clinical task for imaging the subject, and determining the desired dose based on the clinical task.

6. The method of claim 4, further comprising determining a first tube current profile and a second tube current profile to pair with the first tube potential and the second tube potential, respectively, for achieving the desired dose.

7. The method of claim 6, wherein determining the first tube current profile and the second tube current profile comprises selecting a first tube current and a second tube current for the first tube potential and the second tube potential, and adjusting the first tube current relative to the second tube current to provide a highest spectral dose efficiency.

8. The method of claim 1, further comprising receiving an indication of the size of the subject from an operator of the dual energy imaging system.

9. The method of claim 1, further comprising:
   acquiring lower energy projection data and higher energy projection data corresponding to the lower energy x-rays and the higher energy x-rays attenuated respectively by the subject;
   reconstructing an image from the lower energy projection data and the higher energy projection data; and
   outputting the image to one or more of a display device and a storage device.

10. A method for a dual energy imaging system, comprising:
    selecting an imaging protocol for a scan based on a clinical task;
    performing a scout scan of a subject;
    determining a size and a shape of the subject to be imaged;
    automatically determining a dose according to the clinical task for imaging the subject, wherein the size includes a height or a weight of the subject;
    automatically determining a pair of tube potentials to obtain a highest spectral dose efficiency for the size and the shape of the subject;
    determining a pair of tube currents for the pair of tube potentials according to the dose;
    performing a dual energy scan of the subject with the pair of tube currents and the pair of tube potentials; and
    reconstructing an image from dual energy projection data acquired during the dual energy scan.

11. The method of claim 10, further comprising selecting a first tube potential of the pair of tube potentials from a first plurality of tube potentials and a second tube potential of the pair of tube potentials from a second plurality of tube potentials, wherein tube potentials of the first plurality of tube potentials are smaller than tube potentials of the second plurality of tube potentials.

12. The method of claim 11, wherein determining the pair of tube currents comprises determining a first tube current for the first tube potential to provide a first dose and a second tube current for the second tube potential to provide a second dose, wherein the first dose and the second dose add up to the dose.

13. The method of claim 12, further comprising adjusting the first tube current and the second tube current to provide a higher spectral dose efficiency while maintaining the dose.

14. A system, comprising:
    an x-ray source that emits a beam of x-rays toward a subject to be imaged;
    a detector that receives the x-rays attenuated by the subject;
    a data acquisition system (DAS) operably connected to the detector; and
    a computing device operably connected to the DAS and configured with executable instructions in non-transitory memory that when executed cause the computing device to:
      perform a scout scan of the subject to determine a size and a shape of the subject;
      automatically select a first tube potential and a second tube potential according to the size and the shape of the subject and a clinical task, wherein the size includes a height or a weight of the subject;
      control the x-ray source, during a dual energy scan of the subject, with the first tube potential and the second tube potential;
      acquire, via the DAS, lower energy projection data and higher energy projection data corresponding to detected photons generated by the x-ray source at the first tube potential and the second tube potential respectively and attenuated by the subject; and
      reconstruct an image from the lower energy projection data and the higher energy projection data.

15. The system of claim 14, wherein the computing device is further configured with executable instructions that when executed cause the computing device to automatically select the first tube potential and the second tube potential to achieve a highest spectral dose efficiency for the size of the subject.

16. The system of claim 14, wherein the computing device is further configured with executable instructions that when executed cause the computing device to automatically select a first tube current for the first tube potential and a second tube current for the second tube potential based on a target dose for the clinical task.

17. The system of claim 16, wherein the computing device is further configured with executable instructions that when executed cause the computing device to adjust the first tube current and the second tube current to increase a spectral dose efficiency while maintaining the target dose.

18. The system of claim 14, further comprising a display device communicatively coupled to the computing device, wherein the computing device is further configured with executable instructions that when executed cause the computing device to output the image to the display device for display.

\* \* \* \* \*